United States Patent [19]

Altwirth

[11] Patent Number: 5,158,825
[45] Date of Patent: Oct. 27, 1992

[54] ADHERENT INSERT FOR ARTIFICIAL TEETH AND PROCESS OF MANUFACTURING THE INSERT

[76] Inventor: Oskar Altwirth, Oberach 37, A-4950 Altheim, Austria

[21] Appl. No.: 544,938

[22] Filed: Jun. 22, 1990

[30] Foreign Application Priority Data

Jul. 13, 1989 [EP] European Pat. Off. ........ 89890187.1

[51] Int. Cl.⁵ ...................... A61K 6/108; B32B 15/04; C08J 5/10; C08L 1/14
[52] U.S. Cl. .................................... 428/286; 523/120; 523/116; 428/40; 428/290; 428/343; 428/355; 524/28; 524/39; 524/312; 524/388
[58] Field of Search ................. 428/40, 290, 286, 343, 428/355; 523/116, 120; 524/28, 39, 312, 388

[56] References Cited

U.S. PATENT DOCUMENTS 3,740,361  7/1972  Altwirth .............................. 523/120

FOREIGN PATENT DOCUMENTS 2413380  3/1974  Fed. Rep. of Germany .

Primary Examiner—George F. Lesmes
Assistant Examiner—Kathryne E. Shelborne
Attorney, Agent, or Firm—Collard & Roe

[57] ABSTRACT

An adherent insert for artificial teeth consists of a non-woven fabric, which is impregnated with an adhesive.

In order to ensure a strong and persistent adhesiveness, the nonwoven fabric is impregnated with an adhesive which consists of a viscous mixture of alginate and/or carboxymethylcellulose, polyvinyl acetate and a solvent consisting of glycerine triacetate or propylene glycol.

6 Claims, No Drawings

ADHERENT INSERT FOR ARTIFICIAL TEETH AND PROCESS OF MANUFACTURING THE INSERT

BACKGROUND OF THE INVENTION

1. Field of the Invention

This invention relates to an adherent insert for artificial teeth, which insert comprises a nonwoven fabric, which is impregnated with an adhesive, and to a process of manufacturing such adherent inserts.

Description of the Prior Art

In order to increase the adhesiveness and active time of strictly pasty adhesives for artificial teeth, adherent inserts are known, which have been disclosed in DE-C-24 13 380 and consist of a nonwoven fabric, which is impregnated with an adhesive. When the adherent insert has been placed between the denture and the jaw, the fibers of the non-woven fabric virtually reinforce the adhesive and are intended to retard the washing of the adhesive out of the fabric. The nonwoven fabric of the known adherent inserts has been compressed with an adhesive consisting of a dry hydrocolloid powder, which will swell and be activated when it is moistened so that the adhesive can absorb a certain amount of liquid before the adhesive is saturated and the swollen adhesive has a certain adhesiveness. But the adhesive may be washed out of the fabric by mucus and other liquid. For this reason the known adherent inserts which comprise hydrocolloids or other swelling agents are not satisfactory and they cannot retain particularly mandibular dentures, which have rather small surfaces for adhesive contact, in such a manner that a desired safety and bond life are ensured.

SUMMARY OF THE INVENTION

For this reason it is an object of the invention to eliminate said disadvantages and to provide an adherent insert which is of the kind described first hereinbefore and which distinguishes by a particularly effective and persistent adhesiveness.

Another object of the invention is to provide a process for economically manufacturing such adherent inserts.

The first object set forth hereinbefore is accomplished in accordance with the invention resides in that the nonwoven fabric has been impregnated with an adhesive that consists of a viscous, sirupy mixture which contains alginate and/or carboxymethylcellulose or other hydrocolloids, polyvinyl acetate and a physiologically acceptable, water-insoluble solvent, such as glycerine triacetate or propyleneglycol. That adhesive has good adhesive properties because the alginate or the carboxymethylcellulose embedded in the polyvinylacetate prevents a washing of the adhesive out of the fabric and the polyvinyl acetate provides the adherent insert with adhesive properties. Besides, the adhesive exerts a particularly strong vacuum or suction action because when the insert has been placed between the denture and the jaw the adhesive will absorb moisture and will thus be converted to a compact gumlike composition, which is structurally reinforced by the non-woven fabric. That composition is forced against the surfaces for adhesive contact and under the compressive and tensile loads applied during chewing movements and the like will provide regions which are strongly adherent under the action of a vacuum and suction. Together with the adhesiveness of the insert that vacuum and suction action will ensure a surprisingly persistent and strong adhesive bond between the denture and the jaw to ensure a lasting, reliable wearing also of mandibular dentures. For this reason, contrary to other, similar adhesives (DE-C-35 46 367 or EPA 88 89 0202.0, which is no prior publication), alcohol is not used at all and any washing of the adhesive out of the fabric will be minimized. Any alcohol which would be used as a solvent would render the entire adhesive soluble in water. A water-insoluble solvent, which must obviously be physiologically acceptable, cannot be washed out of the fabric and for this reason will ensure the desired persistent bond. It will also prevent the adherent insert from drying up even in a poor package.

If release liners have been placed on both sides of the nonwoven fabric which has been impregnated with the adhesive, the insert will be hygienically protected and can neatly be handled.

In accordance with a further feature of the invention an effective adherent insert is economically manufactured in that a solution of polyvinyl acetate and a physiologically acceptable, water-insoluble solvent, such as glycerin triacetate or propylene glycol, is prepared, alginate and/or carboxymethylcellulose or other hydrocolloids are introduced into said solution, the entire mixture is heated to about 70° C. and is stirred to form a viscous sirupy mixture and that mixture is used to impregnate the entire nonwoven fabric. Most desirably, a solution of about 70% polyvinyl acetate and 30% solvent is prepared and 100 parts by weight of that solution are mixed with 74 parts by weight alginate or carboxymethylcellulose or with 34 parts by weight alginate and 40 parts by weight carboxymethylcellulose. A temperature of at least 70° C. is required for the dissolution of the polyvinyl acetate. At the same temperature, alginate and/or carboxymethyl cellulose are added to that solution. The entire mixture is then stirred in a usual stirring vessel to form a viscous sirupy composition. In a separate vessel, the nonwoven fabric is impregnated with the mixture, also at 70° C., and is subsequently pulled through a stripping system. The resulting adhesive is viscous in a hot state and when cooled down in the nonwoven fabric constitutes a strong, compact, highly adhesive substance, which can hardly be dissolved in water and will produce the desired adhesive and suction action.

It is particularly desirable that in accordance with the invention the nonwoven fabric is impregnated with hot adhesive, the latter is then stripped off to a small thickness, the impregnated nonwoven fabric is then provided with covering films on both sides and the resulting laminate is subsequently punched to form blanks which conform to the denture and are packaged as adherent inserts which are ready for use. To make the adherent inserts a continuous nonwoven web is pulled through the adhesive, which is contained in a tank and is maintained at a temperature of 70° C. The nonwoven web which has absorbed the viscous, hot adhesive is then passed through a stripping system, in which the surplus adhesive is wiped off and the web is sized to a predetermined thickness. The impregnated nonwoven fabric thus obtained may now be covered on both sides with rolled-on covering films and is then sized in a roll system to the required thickness of 0.5 mm. The prefabricated web is then fed to an embossing and punching apparatus, in which suitable blanks are cut, which are subsequently packaged. The economical process which has been described results in adherent inserts which are immediately ready for use and are protected against drying out so that they can be stored for a long time. The adherent inserts are thin. They have the same adhesiveness on both sides and are sufficiently elastic to facilitate their application to the dentures.

The adherent insert in accordance with the invention distinguishes in that the preproduced adhesive is introduced in a hot state into a single layer of a nonwoven fabric and a thin insert is obtained when the adhesive has been set. Because the single-ply nonwoven fabrics are thin, the use of the insert will not increase the height of the bite because the average thickness of the singly-ply nonwoven fabric is not in excess of 0.5 mm whereas conventional inserts have a thickness of 1.5 mm.

Because the hydrocolloids are firmly embedded in the adhesive, the adherent insert in accordance with the invention permits an ingress of liquid only in a small amount into the nonwoven fabric to produce the slight swelling required for the desired suction action. The persistence of the suction action for a long time is due to the fact that the liquids which produce the suction action are taken up by the adhesive only in small amounts. As a result, the necessary ingress of some liquid will be ensured but a washing of the adhesive out of the nonwoven fabric will be prevented.

Because the nonwoven fabric is not impregnated with an adhesive which contains alcohol as a solvent and which obviously cannot bond to the nonwoven fabric but will be washed out of the fabric in use, but the nonwoven fabric is impregnated at an elevated temperature with a viscous substance, which is solidified and becomes compact as it is allowed to cool and is thus bonded to the nonwoven fabric, so that a particularly strong and persistent adhesive and suction action is ensured.

I claim:

1. An adherent insert for artificial teeth, comprising a nonwoven fabric impregnated with a composition comprising polyvinyl acetate, at least one hydrocolloid embedded in said polyvinyl acetate, and a physiologically acceptable, water-insoluble solvent free of alcohol and forming, at an elevated temperature, with said polyvinyl acetate and said hydrocolloid a syrupy viscous adhesive composition.

2. The adherent insert set forth in claim 1, wherein said solvent is selected from the group consisting of glycerine triacetate and propylene glycol.

3. The adherent insert set forth in claim 1, wherein said hydrocolloid is selected from the group consisting of alginate and carboxymethylcellulose.

4. The adherent insert set forth in claim 2, wherein said composition comprises about 74 parts by weight of said hydrocolloid per 70 parts by weight polyvinyl acetate.

5. The adherent insert set forth in claim 3, wherein said composition comprises about 34 parts by weight alginate and about 40 parts by weight carboxymethylcellulose per 70 parts by weight of polyvinyl acetate.

6. The adherent insert set forth in claim 1, wherein said nonwoven fabric is covered on both sides with release liners.

* * * * *